United States Patent [19]

Hatanaka et al.

[11] Patent Number: 5,409,701
[45] Date of Patent: Apr. 25, 1995

[54] FR901451 SUBSTANCE, PROCESS FOR PREPARATION THEREOF AND USE THEREOF

[75] Inventors: Hiroshi Hatanaka, Moriya; Shigehiro Takase, Ishioka; Takashi Fujita, Tsuchiura; Masanori Okamoto; Masakuni Okuhara, both of Tsukuba, all of Japan

[73] Assignee: Fujisawa Pharmaceutical Co., Ltd., Osaka, Japan

[21] Appl. No.: 178,245
[22] PCT Filed: Jul. 14, 1992
[86] PCT No.: PCT/JP92/00894
  § 371 Date: Jan. 24, 1994
  § 102(e) Date: Jan. 24, 1994
[87] PCT Pub. No.: WO93/02203
  PCT Pub. Date: Feb. 4, 1993

[30] Foreign Application Priority Data

Jul. 22, 1991 [GB] United Kingdom ................. 9115811

[51] Int. Cl.⁶ .......................... C12P 1/04; C12P 21/00; A61K 35/74
[52] U.S. Cl. .................... 435/118; 435/71.1; 435/252.1; 435/822
[58] Field of Search ................... 435/252.1, 71.1, 822; 424/118

[56] References Cited

U.S. PATENT DOCUMENTS 4,971,965 11/1990 Ono et al. .................... 435/252.1

Primary Examiner—Herbert J. Lilling
Attorney, Agent, or Firm—Oblon, Spivak, McClelland, Maier & Neustadt

[57] ABSTRACT

A new FR901451 substance which is produced by culturing a FR901451 substance-producing strain of the genus Flexibacter in a nutrient medium, this new substance possessing a human leukocyte elastase-inhibiting activity.

10 Claims, 3 Drawing Sheets

FR901451 SUBSTANCE, PROCESS FOR PREPARATION THEREOF AND USE THEREOF

TECHNICAL FIELD

This invention relates to a new FR901451 substance. More particularly, this invention relates to a new FR901451 substance and its pharmaceutically acceptable salts which have a human leukocyte elastase-inhibiting activity, to a process for preparation thereof, and to a pharmaceutical composition comprising the same and to a method of use thereof.

DISCLOSURE OF INVENTION

The FR901451 substance can be produced by culturing a FR901451 substance-producing strain of the genus Flexibacter in a nutrient medium.

THE MICROORGANISM

The microorganism which can be used for the production of FR901451 substance is a FR901451 substance-producing strain belonging to the genus Flexibacter, among which Flexibacter sp. No. 758 has been newly isolated from a soil sample collected at Hirono-cho, Chiba-ken, Japan.

A lyophilized sample of the newly isolated Flexibacter sp. No. 758 has been deposited with International Depository Authority under the Budapest Treaty, the Fermentation Research Institute, Agency of Industrial Science and Technology (1-3, Higashi 1 chome, Tsukuba-shi, Ibaraki-ken, 305 Japan) under the accession number of FERM BP-3420 (the deposited date: May 21, 1991).

It is to be understood that the production of the novel FR901451 substance is not limited to the use of the particular organism described herein, which is given for the illustrative purpose only. This invention also includes the use of any mutants which are capable of producing FR901451 substance including natural mutants as well as artificial mutants which can be produced from the described organism by conventional means such as irradiation of X-ray, ultra-violet radiation, treatment with N-methyl-N'-nitro-N-nitrosoguanidine, 2-aminopurine, and the like.

The Flexibacter sp. No. 758 has the following morphological, cultural, biological and physiological characteristics.

The methods described in Bergey's Manual of Systematic Bacteriology (Volume 3) were employed principally for this taxonomic study.

(1) Morphological characteristics:

Morphological observation of strain No. 758 was carried out by the optical microscope with cells cultured on nutrient agar and Cytophaga agar at 30° C. for 24 hours. Strain No. 758 was a gram-negative bacterium. It was slender rods or sometimes filaments, motile by gliding. It was about 0.8–1.0×15–18 μm in size. Colonies of strain No. 758 were orange yellow, circular, convex, and entire-edged on nutrient agar. Results were shown in Table 1.

(2) Physiological characteristics:

Physiological Characteristics of strain No. 758 were summarized in Table 2. The growth temperature was from 17° C. to 44° C. Strain No. 758 was oxidase positive, catalase positive, flexirubin reaction positive. Nitrate was reduced to nitrite is strain hydrolized gelatin, casein and esculin. Starch hydrolysis was negative. It was chitinase and cellulase negative. Decomposing ability of agar and alginat was negative. The mole percent G+C of the DNA was 49.8%. Acid formation was observed from D-glucose, D-xylose, D-galactose, sucrose, lactose and maltose. The following compounds were utilized as a sole carbon source: Namely, D-glucose, L-arabinose, D-xylose, D-fructose, D-mannose, D-galactose, sucrose, lactose and maltose. D-mannitol and sorbitol were not utilized.

(3) Identification:

According to Bergey's Manual of Systematic Bacteriology (Volume 3), strain No. 758 was considered to belong to genus Flexibacter from those characteristics described above. Then, we identified this strain as one strain of Flexibacter and named it Flexibacter sp. No. 758.

TABLE 1

| Morphological characteristics of strain No. 758 | |
| --- | --- |
| gram stain | negative |
| color of colony | orange yellow |
| cell shape | slender rods |
| cell size | 0.8–1.0 × 15–18 μm |
| motility | gliding |
| spore formation | negative |

TABLE 2

| Physiological characteristics of strain No. 758 | |
| --- | --- |
| conditions | characteristics |
| growth temperature | 17–44° C. |
| growth in air | positive |
| growth on Macconkey agar (DIFO marine agar 2216) | negative |
| flexirubin reaction | positive |
| catalase | positive (weak) |
| oxidase | positive |
| tolerance to NaCl (%) | 0–2 |
| H$_2$S (SIM) | negative |
| simmons citrate | negative |
| nitrate reduction | positive |
| indol | negative |
| gelatin liquefaction | positive |
| casein hydrolysis | positive (weak) |
| esculin hydrolysis | positive |
| starch hydrolysis | negative |
| Tween 80 hydrolysis | negative |
| maltose | positive |
| salicine | negative |
| utilization of | |
| D-glucose | positive |
| L-arabinose | positive |
| D-xylose | positive |
| D-fructose | positive |
| D-mannose | positive |
| D-galactose | positive |
| D-mannitol | negative |
| sucrose | positive |
| lacotse | positive |
| maltose | positive |
| sorbitol | negative |
| degradation of | |
| colloidal chitin | negative |
| carboxylmethylcellulose | negative |
| agar | negative |
| alginate | negative |
| ONPG test | positive |
| DNase | positive |
| lysin decarboxylase | negative |
| arginine dihydrolase | positive (weak) |
| ornitine decarboxylase | negative |
| G + C content of DNA | 49.8% |
| acid from | |
| D-glucose | positive |
| D-xylose | positive |
| D-fructose | negative |
| D-galactose | positive |
| D-mannitol | positive |

TABLE 2-continued

Physiological characteristics of strain No. 758

| conditions | characteristics |
| --- | --- |
| sucrose | positive |
| lactose | positive |

FR901451 SUBSTANCE

The FR901451 substance is produced when a FR901451 substance-producing strain belonging to the genus Flexibacter is grown in a nutrient medium containing sources of assimilable carbon and nitrogen under aerobic conditions (e.g. shaking culture, submerged culture, etc.). The medium may be either synthetic, semi-synthetic or natural.

Preferred carbon sources may be glucose, mannose, glycerin, molasses, starch, starch hydrolysate and so on, and preferred nitrogen sources may be meat extract, casein hydrolysate, peptone, gluten meal, corn meal, cottonseed meal, soybean meal, corn steep liquor, dried yeast, ammonium phosphate, ammonium sulfate, urea and so on. There may also be incorporated inorganic salts such as the phosphates, chlorides and other salts of metals, e.g. disodium hydrogen phosphate, potassium dihydrogen phosphate, calcium carbonate, ferrous sulfate magnesium sulfate, copper sulfate, zinc sulfate, manganese chloride, magnesium chloride, etc. If copious foaming is encountered during fermentation, a deforming agent such as vegetable oils, e.g. soybean oil, linseed oil, etc., higher alcohols, e.g. octadecanol, may be added in suitable amounts.

The fermentation is preferably conducted at around 30° C. for 30 to 100 hours.

From the above-mentioned fermentation conditions, the optimum set of conditions is selected according to the characteristics of the strain of microorganism employed.

Since a major portion of the FR901451 substance thus produced in the cultured broth is present extracellularly, there is added a suitable solvent such as acetone to the cultured broth.

The resultant mixture is filtered with the aid of diatomaseous each and the desired compound is then separated and purified from the filtrate by the procedure employed commonly in the production of antibiotics in general. For example, there may be employed such procedures as concentration under reduced pressure, freeze drying, solvent extraction, pH adjustment, treatment with an anion exchange resin, cation exchange resin, nonionic adsorbent resin, etc., treatment with an adsorbent agent such as activated carbon, silicic acid, silica gel or alumina, crystallization, and recrystallization, either singly or in an optional combination.

The FR901451 substance produced in the cultured broth can be isolated in its free form or if desired, in the form of a pharmaceutically acceptable salt. For isolating the substance in the form of a pharmaceutically acceptable salt, the desired compound obtained from the cultured broth extract is treated with a base such as an inorganic base, e.g. an alkali metal compound (e.g. sodium hydroxide, potassium hydroxide, etc.), an alkaline earth metal compound (e.g. calcium hydroxide, magnesium hydroxide, etc.), an inorganic base, e.g. ammonia etc., an organic base (e.g. triethylamine, dicyclohexylamine, etc.) or an acid such as an inorganic acid (e.g. hydrochloric acid, sulfuric acid, phosphoric acid, etc.) or an organic acid (e.g. formic acid, acetic acid, p-toluenesulfonic acid, citric acid, oxalic acid, etc.), whereby the corresponding salt of FR901451 substance can be obtained.

The salt of FR901451 substance thus obtained can be reconverted to free FR901451 substance in the per se conventional manner.

The FR901451 substance is a new substance and has the following physico-chemical properties.

Physico-chemical properties of FR901451 substance:
  Appearance: White powder
  Color reaction: Positive; Cerium sulfate, Iodine vapor, Ehrlich, Ninhydrin Negative; Molish
  Solubility: Soluble; Water, Methanol, Dimethyl sulfoxide Sparingly soluble; Acetone Insoluble; Ethyl acetate
  Melting point: 243°–245° C. (decomposition)
  Specific rotation: $[\alpha]_D^{23} -15°$ (C=0.65, H$_2$O)
  Ultraviolet absorption spectrum: $\lambda_{max}^{MeOH}$ nm ($\epsilon$) 275 (4300), 281 (4500), 290 (3900)
  Molecular formula: $C_{60}H_{79}N_{13}O_{18}$
  Elemental analysis: Calcd. for $C_{60}H_{79}N_{13}O_{18} \cdot 10H_2O$ C 49.68, H 6.88, N 12.55 Found: C 49.95, H 6.28, N 12.42
  Molecular weight : FAB-MS m/z 1270 (M+H)+
  Thin layer chromatography:

| Stationary phase | Developing solvent | Rf value |
| --- | --- | --- |
| Silica gel (Merck) | CHCl$_3$:MeOH:NH$_4$OH (15:11:5) | 0.60 |
| RP-18 (Merck) | 70% aq. Methanol | 0.32 |

FT-Infrared absorption spectrum (FIG. 1):
  KBr 3390, 3070, 2970, 2880, 1740, 1660, 1530,
  $\nu$max 1450, 1410, 1380, 1350, 1250, 1190, 1110, 1080, 1010, 750, 700, 670, 660, 620, 600 cm$^{-1}$

| $^1$H Nuclear Magnetic Resonance Spectrum (FIG. 2) (400 MHz, D$_2$O) $\delta$ | |
| --- | --- |
| 7.70 | (1H, d, J=7Hz) |
| 7.52 | (1H, d, J=7.5Hz) |
| 7.44–7.23 | (7H, m) |
| 7.22 | (1H, s) |
| 5.59 | (1H, q, J=7Hz) |
| 4.94 | (1H, t, J=4.5Hz) |
| 4.85–4.74 | (3H, m) |
| 4.58 | (1H, dd, J=6Hz, 10Hz) |
| 4.45–4.35 | (3H, m) |
| 4.30 | (1H, dd, J=4Hz, 7Hz) |
| 4.07 | (1H, m) |
| 3.99 | (1H, dd, J=10Hz, 4.5Hz) |
| 3.66–3.50 | (3H, m) |
| 3.44–3.25 | (4H, m) |
| 3.16–2.93 | (4H, m) |
| 2.87 | (1H, d, J=18Hz) |
| 2.80–2.68 | (2H, m) |
| 2.56–2.48 | (2H, m) |
| 2.08 | (1H, dd, J=16Hz, 4Hz) |
| 1.87–1.53 | (9H, m) |
| 1.43 | (3H, d, J=7Hz) |
| 1.30 | (3H, d, J=6.5Hz) |
| 1.45–1.17 | (4H, m) |
| 0.95 | (3H, d, J=6Hz) |
| 0.84 | (3H, d, J=6Hz) |

| $^{13}$C Nuclear Magnetic Resonance Spectrum (FIG. 3): (100 MHz, D$_2$O) $\delta$ | |
| --- | --- |
| 177.2 (s) | 54.1 (d) |
| 176.5 (s) | 53.8 (d) |
| 174.6 (s) | 53.2 (d) |

| ¹³C Nuclear Magnetic Resonance Spectrum (FIG. 3): | |
|---|---|
| (100 MHz, D₂O) δ | |
| 174.2 (s) | 53.1 (d) |
| 174.0 (s) | 52.9 (d) |
| 173.2 (s) | 52.8 (d) |
| 173.0 (s) | 49.5 (d) |
| 172.8 (s) | 48.6 (t) |
| 172.6 (s) | 40.1 (t) |
| 172.5 (s) | 39.6 (t) |
| 172.1 (s) | 39.4 (t) |
| 171.7 (s) | 38.9 (t) |
| 171.4 (s) | 35.3 (t) |
| 170.3 (s) | 34.8 (t) |
| 137.2 (s) | 31.7 (t) |
| 136.0 (s) | 31.4 (t) |
| 130.0 (d) × 2 | 28.8 (t) |
| 129.8 (d) × 2 | 26.6 (t) |
| 128.5 (d) | 25.1 (d) |
| 127.8 (s) | 23.2 (q) |
| 125.5 (d) | 23.2 (t) |
| 123.2 (d) | 23.1 (t) |
| 120.9 (d) | 20.8 (q) |
| 118.7 (d) | 19.4 (q) |
| 113.1 (d) | 18.3 (q) |
| 108.8 (s) | |
| 73.3 (d) | |
| 69.7 (d) | |
| 64.3 (t) | |
| 62.1 (d) | |
| 60.9 (d) | |
| 57.1 (d) | |
| 56.0 (d) | |

A pharmaceutically acceptable salt of the FR901451 substance may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt, pyridine salt or the like.

The FR901451 substance and pharmaceutically acceptable salt thereof have a human leukocyte elastase-inhibiting activity and is useful as human leukocyte elastase inhibitors for treating or preventing degenerative diseases, for example, pulmonary emphysema, atherosclerosis, rheumatoid arthritis, arthrosclerosis, osteoarthritis, psoriasis, pancreatitis, periodontosis, pulmonary fibrosis, cystic fibrosis, chronic bronchitis, bronchiectasia, diffuse panbronchiolitis, respiratory injury, adult respiratory distress syndrome and the like, and further is useful for treatment or prevention of asthma, graft rejection nephritis, hydroa, disseminated intravascular coagulation, shock, systemic lupus erythematosus, clone disease, ischemia-reperfusion injury, chronic obstructive pulmonary disease (COPD), premature rupture of the membrane (PROM), corneal sarring or fibroblast proliferation (ocular coagulation, burns, mechanical and chemical injury, kerato-conjunctivitis, etc.), and sepsis.

In order to illustrate the usefulness of the FR901451 substance and its pharmaceuticallyacceptable salt, pharmacological test data thereof are shown below.

1. Protease Inhibition assay

A buffer used throughout the assay was 0.1M HEPES (N- (2-hydroxyethyl )piperazine-N'-2-ethanesulfonic acid ) containing 0.5M NaCl, pH 7.5. Twenty-five microliter of 2 mM methoxy-succinyl-(Ala)₂-pro-Val-p-nitroanilide (100 mM of dimethyl sulfoxide solution was diluted in the buffer) and 50 μl of sample (10 μl of sample in organic solvent was diluted 5-fold in the buffer) were mixed in wells of 96well-microtiter plate. An absorbance of the mixture in wavelength at 415 nm was measured by a microplate reader (Corona Electric Co., Ibaraki, Japan). After the measurement 25 μl of 6 ug/ml human sputum elastase (HSE, Elastin Products Company Inc., MO, USA) was added and allowed to stand for 30 minutes at room temperature. Then, the absorbance at 415 nm was measured. Percent inhibition by drug was determined by 100×(1−"r" inhibitor present/"r" inhibitor absent), where "r" is absorbance after 30 min incubation minus absorbance before enzyme addition. Effects of inhibitors against other proteases were assayed similarly using N-succinyl-(Ala)₃-p-nitroanilide for porcine pancreas elastase (Type IV, 5 ug/ml final), N-alpha-benzoyl-Arg-p-nitroanilide for bovine pancreas trypsin (Type I, 16 ug/ml final), methoxysuccinyl-(Ala)₂-Pro-Met-p-nitroanilide for bovine pancreas chymotrypsin (Type II, 1.5 ug/ml final). All substrates and proteases except HSE were purchased from Sigma Chemicals Co.

| | Inhibitory effects of FR901451 substance on several serine protease activity | | | |
|---|---|---|---|---|
| Inhibitor (μg/ml) | Human sputum elastase | Porcine pancreas elastase | Trypsin (bovine) | Chymotrypsin (bovine) |
| FR901451 substance | 2.3 × 10⁻⁷M | 2.7 × 10⁻⁷M | 7.9 × 10⁻⁵M | 1.1 × 10⁻⁷M |

Each value was expressed as 50% inhibitory concentration.

2. The effect of FR901451 substance on experimentally induced emphysema.

A. Methods

Male golden Syrian hamsters, weighing approximately 120 g, were obtained from Japan SLC Inc.

Porcine Pancreatic Elastase (PPE) was purchased from Sigma Chemicals.

Dialferin ® was purchased from Japan Roche Inc.

Hamsters were anesthetized intraperitoneally with Pentobarbital.

FR901451 substance (1, 10, 100, 1000 μg/site) in 0.2 ml of saline was instilled intratracheally through the oral cavity, 5 minutes before 100 μg/site of PPE in 0.2 ml of saline instillation.

Three weeks after PPE instillation, the hamsters were anesthetized with Pentobarbital.

Respiratory mechanics were studied in supine hamsters using a whole-body, constant-volume, variable-pressure plethysmograph to measure volume.

A water-filled esophageal catheter was used to estimate pleural pressure.

Quasi-static deflation pressure-volume (P-V) curves were obtained by intraperitoneally administered Dialferin ® to suppress spontaneous breathing, inflating the lungs to a transpulmonary pressure (PL) of 30 cm H₂O, permitting slow deflation to a PL of 0 cm H₂O and gently aspirating to a PL of −20 cm H₂O.

Quasi-static lung compliance (Cst) was defined as the slope of the steep portion of the deflation P-V curve in the mid-volume range.

Vital capacity was defined as the difference in lung volume between TLC25 (volume at PL=25 cm $H_2O$) and RV-20 (volume at PL=−20 cm $H_2O$).

B. Results

Pretreatment of FR901451 substance could protect against PPE-induced increases in lung mechanics in a dose dependent manner as shown in table 1.

| Effect of FR901451 Substance on PPE Induced Emphysema in Hamsters | | | |
|---|---|---|---|
| | | Cst (ml/cm $H_2O$) | VC (ml) |
| NORMAL | | 0.45 ± 0.01 *** | 4.71 ± 0.05 *** |
| CONTROL | | 1.05 ± 0.06 | 7.23 ± 0.20 |
| FR901451 SUBSTANCE | 1 μg/site | 1.06 ± 0.05 (−1%) | 6.91 ± 0.02 (14%) |
| | 10 μg/site | 1.04 ± 0.04 (2%) | 6.99 ± 0.15 (11%) |
| | 100 μg/site | 0.88 ± 0.03 (29%) * | 6.25 ± 0.18 (40%) ** |
| | 1000 μg/site | 0.71 ± 0.05 (56%) *** | 5.82 ± 0.24 (57%) *** |

Cst = Quasi Static Lung Compliance
VC = Vital Capacity
(%) = inhibition
*$P < 0.05$, $P < 0.01$, *$P < 0.001$ VS Control Pharmaceutical compositions of this invention can be used in a conventional pharmaceutical forms such as injections, inhalations, powders, fine granules, granules, tablets, dragee, microcapsules, capsules, suppository, solution, suspension, emulsion syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 100 mg to 10 g as the object compound or its pharmaceutically acceptable salt, preferably 1 g to 5 g on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

EXAMPLE

An aqueous seed medium (120 ml) containing 0.5% of yeast extract, 1.0% polypeptone and 0.5% NaCL was poured into each of three 500 ml Erlenmeyer flasks, and sterilized at 120° C. for 30 minutes. A loopful of Flexibacter sp. No. 758 on mature slant culture was inoculated to each of the seed medium. The flasks were shaken on a rotary shaker at 30° C. for 1 day. The resultant seed culture was inoculated to 20l of sterile fermentation medium consist of 4.8% soluble starch, 1.6% corn steep liquor, 0.16% $(NH_4)_2SO_4$, 0.0096% $MgSO_4.7H_2O$ and 0.32% $CaCO_3$ (PH 7.0) in 30l stainless steel jar-fermentor. The fermentation was carried out at 30° C. for 2 days under aeration of 20l/min and agitation of 180 rpm.

An amount of FR901451 substance in the fermentation broth was quantified by elastase inhibition assay in vitro. The sample for the assay was prepared as follows;

An equal volume of acetone was added to a broth with vigorous stirring and stand for an hour, and then filtered. The filtrate was concentrated under reduced pressure to an appropriate volume. The elastase inhibition assay was as described before.

An equal volumn of acetone was added to a 100l of the fermentation broth with stirring and stood for an hour and then filtered. The filtrate was concentrated to remove the acetone under reduced pressure. Thus obtained concentrate (100l) was passed through a column of polymeric adsorbent, Diaion HP-20 (trade name, made by Mitsubishi Chemical Industries Limited, 3l). The column was washed with 9l of water and eluted with 20l of methanol. The eluate was concentrated under reduced pressure and resulted 4l of the aqueous solution was adjusted to pH 2.0 with 6N HCl, and then washed with 4l of ethyl acetate. The water layer separated was then adjusted to pH 7.0 with 6N NaOH solution and extracted with 2l of n-butanol. The butanol extract was concentrated under reduced pressure to give a 3.2 g of oily residue. The residue was applied to a column chromatography on silica gel (Kiesel gel 60, 70–230 mesh, Merck, 450 ml). The column was washed with 1.5l of isopropanol and 1.5l of 90% aq. isopropanol solution and the active substance was eluted from the column with 1.5l of 80% aq. isopropanol solution. The eluate was concentrated and applied to a column chromatography on reverse phase silica, YMC-ODS-AM (Yamamura Chemical Institute, 300 ml), prepacked with 50% aq. methanol.

The active sub,stances were eluted from the column stepwisely by solvent systems of 50%, 60% and 70% aq. methanol. First 340 ml eluate of the 50% aq. methanol fraction was discarded and next 120 ml of the eluate containing FR901451 substance was collected.

The 50% aq. methanol fraction containing FR901451 substance was concentrated to dryness and redissolved in 3 ml of n-butanol-ethanol-water (4:1:1, v/v) solution. The solution was subjected to a column chromatography on silica gel (85 ml), prepacked with n-butanol-ethanol-water (4:1:1, v/v) and developed with the same solvent. First 160 ml the eluate was discarded and the next 40 ml eluted containing the objective substance was collected. The solution of the active substance was concentrated under reduced pressure to give 37 mg of FR901451 substance as pure powder.

INDUSTRIAL APPLICABILITY

The FR901451 substance of this invention can be used as a human leukocyte elastase inhibitor.

We claim:

1. A FR901451 substance having the following physico-chemical properties and its pharmaceutically acceptable salt:

Appearance: White powder

Color reaction: Positive; Cerium sulfate, Iodine vapor, Ehrlich, Ninhydrin Negative; Molish
Solubility: Soluble; Water, Methanol, Dimethyl sulfoxide Sparingly soluble; Acetone Insoluble; Ethyl acetate
Melting point: 243°–245° C. (decomposition)
Specific rotation: $[\alpha]_D^{23} -15°$ (C=0.65, $H_2O$)
Ultraviolet absorption spectrum: $\lambda_{max}^{MeOH}$ nm ($\epsilon$) 275 (4300), 281 (4500), 290 (3900)
Molecular formula: $C_{60}H_{79}N_{13}O_{18}$
Elemental analysis: Calcd. for $C_{60}H_{79}N_{13}O_{18}\cdot 10H_2O$ C 49.68, H 6.88, N 12.55 Found: C 49.95, H 6.28, N 12.42
Molecular weight : FAB-MS m/z 1270 $(M+H)^+$
Thin layer chromatography:

| Stationary phase | Developing solvent | Rf value |
| --- | --- | --- |
| Silica gel (Merck) | $CHCl_3$:MeOH:$NH_4OH$ (15:11:5) | 0.60 |
| RP-18 (Merck) | 70% aq. Methanol | 0.32 |

Figure 1:
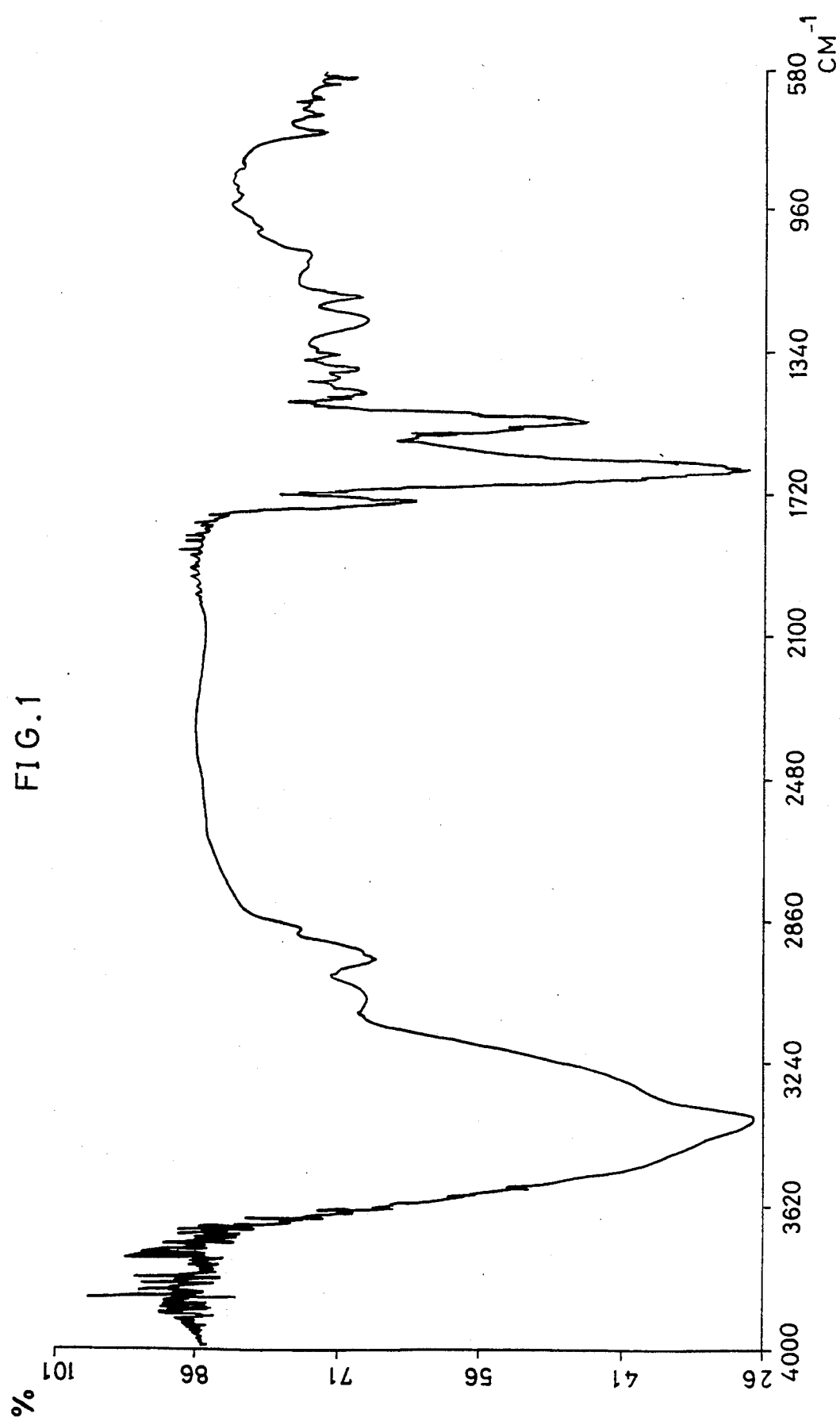
FIG. 1 shows FT-Infrared absorption spectrum of a FR901451 substance.

FT-Infrared absorption spectrum (FIG. 1):
KBr 3390, 3070, 2970, 2880, 1740, 1660, 1530, $\nu$max 1450, 1410, 1380, 1350, 1250, 1190, 1110, 1080, 1010, 750, 700, 670, 660, 620, 600 cm$^{-1}$

Figure 2:
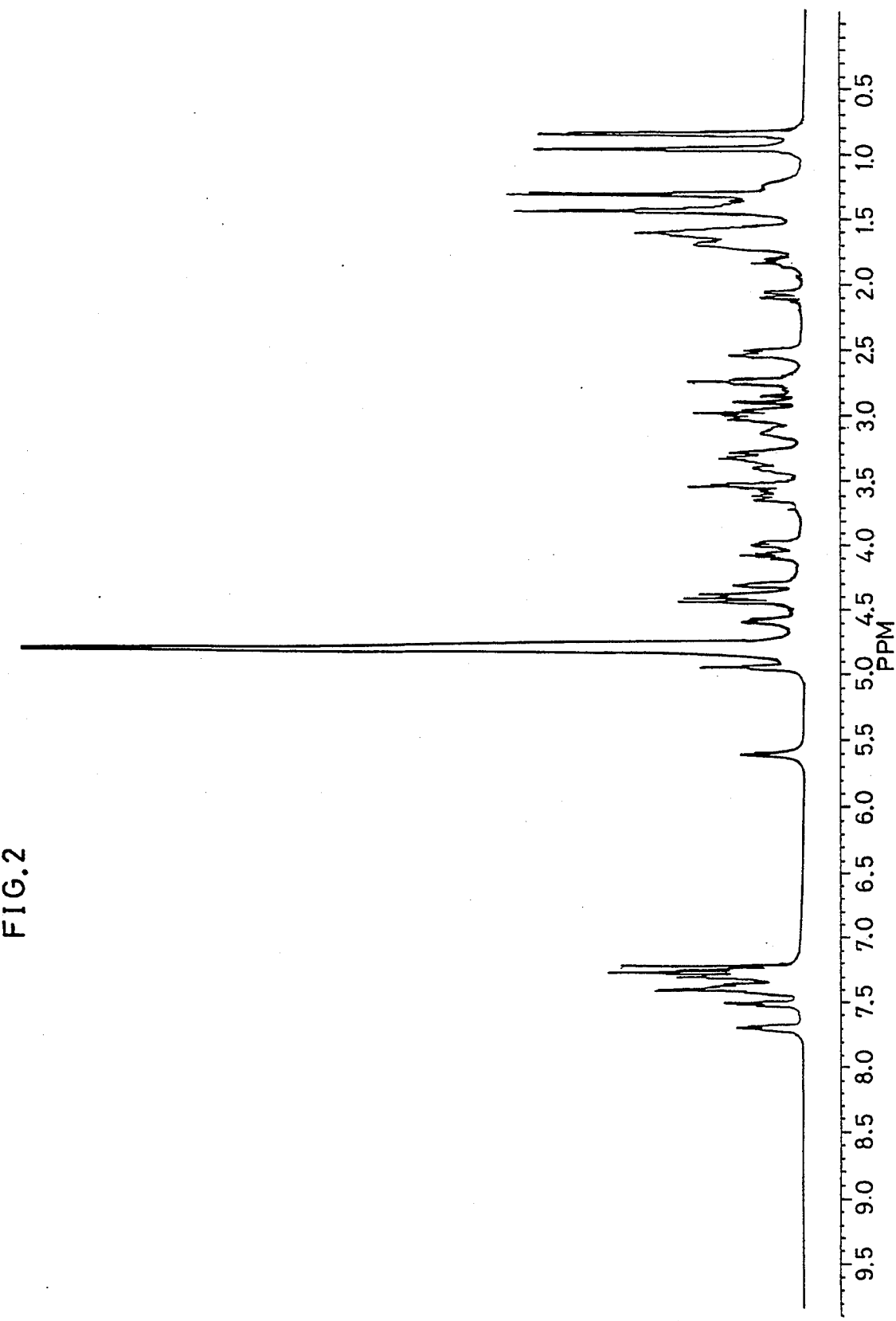
FIG. 2 shows $^1H$ Nuclear magnetic resonance spectrum of the same and FIG. 3 shows $^{13}C$ Nuclear magnetic resonance spectrum of the same.

| $^1$H Nuclear Magnetic Resonance Spectrum (FIG. 2) (400 MHz, $D_2O$) δ | |
| --- | --- |
| 7.70 | (1H, d, J=7Hz) |
| 7.52 | (1H, d, J=7.5Hz) |
| 7.44–7.23 | (7H, m) |
| 7.22 | (1H, s) |
| 5.59 | (1H, q, J=7Hz) |
| 4.94 | (1H, t, J=4.5Hz) |
| 4.85–4.74 | (3H, m) |
| 4.58 | (1H, dd, J=6Hz, 10Hz) |
| 4.45–4.35 | (3H, m) |
| 4.30 | (1H, dd, J=4Hz, 7Hz) |
| 4.07 | (1H, m) |
| 3.99 | (1H, dd, J=10Hz, 4.5Hz) |
| 3.66–3.50 | (3H, m) |
| 3.44–3.25 | (4H, m) |
| 3.16–2.93 | (4H, m) |
| 2.87 | (1H, d, J=18Hz) |
| 2.80–2.68 | (2H, m) |
| 2.56–2.48 | (2H, m) |
| 2.08 | (1H, dd, J=16Hz, 4Hz) |
| 1.87–1.53 | (9H, m) |
| 1.43 | (3H, d, J=7Hz) |
| 1.30 | (3H, d, J=6.5Hz) |
| 1.45–1.17 | (4H, m) |
| 0.95 | (3H, d, J=6Hz) |
| 0.84 | (3H, d, J=6Hz) |

Figure 3:
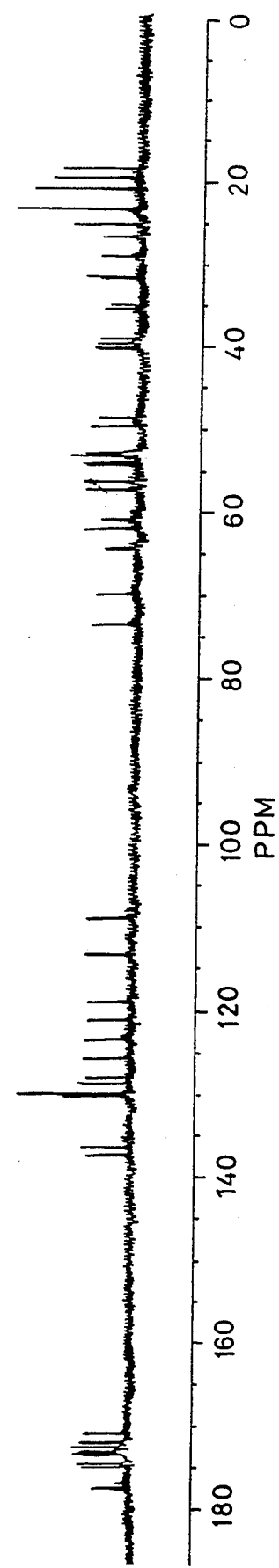

| $^{13}$C Nuclear Magnetic Resonance Spectrum (FIG. 3) (100 MHz, $D_2O$) δ | | | |
| --- | --- | --- | --- |
| 177.2 (s) | 127.8 (s) | 52.8 (d) | 18.3 (q) |
| 176.5 (s) | 125.5 (d) | 49.5 (d) | |
| 174.6 (s) | 123.2 (d) | 48.6 (t) | |
| 174.2 (s) | 120.9 (d) | 40.1 (t) | |
| 174.0 (s) | 118.7 (d) | 39.6 (t) | |
| 173.2 (s) | 113.1 (d) | 39.4 (t) | |
| 173.0 (s) | 108.8 (s) | 38.9 (t) | |
| 172.8 (s) | 73.3 (d) | 35.3 (t) | |
| 172.6 (s) | 69.7 (d) | 34.8 (t) | |
| 172.5 (s) | 64.3 (t) | 31.7 (t) | |
| 172.1 (s) | 62.1 (d) | 31.4 (t) | |
| 171.7 (s) | 60.9 (d) | 28.8 (t) | |
| 171.4 (s) | 57.1 (d) | 26.6 (t) | |
| 170.3 (s) | 56.0 (d) | 25.1 (d) | |
| 137.2 (s) | 54.1 (d) | 23.2 (q) | |
| 136.0 (s) | 53.8 (d) | 23.2 (t) | |
| 130.0 (d) × 2 | 53.2 (d) | 23.1 (t) | |
| 129.8 (d) × 2 | 53.1 (d) | 20.8 (q) | |
| 128.5 (d) | 52.9 (d) | 19.4 (q) | |

2. A process for preparing FR901451 substance or its pharmaceutically acceptable salt which comprises culturing a FR901451 substance-producing strain belonging to the genus Flexibacter in a nutrient medium and isolating FR901451 substance or its pharmaceutically acceptable salt from the cultured broth, wherein said FR901451 substance-producing strain belonging to the genus Flexibacter is Flexibacter sp. No. 758, BP-3420.

3. A pharmaceutical composition comprising as an effective ingredient a FR901451 substance as defined in claim 1 or its pharmaceutically acceptable salt in association with a pharmaceutically acceptable carrier or excipient.

4. A human leukocyte elastase inhibitor comprising as an effective ingredient a FR901451 substance as defined in claim 1 or its pharmaceutically acceptable salt in association with a pharmaceutically acceptable carrier or excipient.

5. A pharmaceutical composition for treatment or prevention of a degenerative disease selected from the group consisting of plumonary emphysema, atherosclerosis, rheumatoid arthritis, arthrosclerosis, osteoarthritis, psoriasis, pancreatitis, periodontosis, pulmonary fibrosis, cystic fibrosis, chronic bronchitis, bronchiectasia, diffuse panbronchiolitis, respiratory injury, and adult respiratory distress syndrome comprising as an effective ingredient a FR901451 substance as defined in claim 1 or its pharmaceutically acceptable salt in association with a pharmaceutically acceptable carrier or excipient.

6. A pharmaceutical composition for treatment or prevention of graft rejection comprising as an effective ingredient a FR901451 substance as defined in claim 1 or its pharmaceutically acceptable salt in association with a pharmaceutically acceptable carrier or excipient.

7. A pharmaceutical composition for treatment of nephritis, sepsis, hydroa, disseminated intravascular coagulation, shock, systemic lupus erythematosus clone disease, ischemia-reperfusion injury, chronic obstructive pulmonary disease (COPD), premature rupture of the membrane (PROM), corneal sarring or fibroblast proliferation or asthma comprising as an effective ingredient a FR901451 substance as defined in claim 1 or its pharmaceutically acceptable salt in association with a pharmaceutically acceptable carrier or excipient.

8. A method of treating or preventing degenerative disease selected from the group consisting of pulmonary emphysema, atherosclerosis, rheumatoid arthritis, arthrosclerosis, osteoarthritis, psoriasis, pancreatitis, periodontosis, pulmonary fibrosis, cystic fibrosis, chronic bronchitis, bronchiectasia, diffuse panbronchiolitis, respiratory injury, and adult respiratory distress syndrome in a subject in need thereof which comprises administering to the subject an effective amount of a FR901451 substance as defined in claim 1 or its pharmaceutically acceptable salt.

9. A method of treating or preventing graft rejection in a subject in need thereof which comprises administering to the subject an effective amount of a FR901451 substance as defined in claim 1 or its pharmaceutically acceptable salt.

10. A method of treating or preventing nephritis, sepsis, hydroa, disseminated intravascular coagulation, shock, systemic lupus erythematosus, clone disease, ischemia-reperfusion injury, chronic obstructive pulmonary disease (COPD), premature rupture of the membrane (PROM), corneal sarring or fibroblast proliferation or asthma in a subject in need thereof which comprises administering to the subject an effective amount of a FR901451 substance as defined in claim 1 or its pharmaceutically acceptable salt.

* * * * *